US012788871B2

(12) United States Patent
Demizu et al.

(10) Patent No.: US 12,788,871 B2
(45) Date of Patent: Nov. 10, 2026

(54) INFUSION CARTRIDGE, INFUSION PUMP, AND METHOD FOR MANUFACTURING INFUSION CARTRIDGE

(71) Applicant: TERUMO KABUSHIKI KAISHA, Tokyo (JP)

(72) Inventors: Shun Demizu, Hadano (JP); Koshi Sano, Minami-Alps (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 449 days.

(21) Appl. No.: 18/435,657

(22) Filed: Feb. 7, 2024

(65) Prior Publication Data

US 2024/0173470 A1 May 30, 2024

Related U.S. Application Data

(63) Continuation of application No. PCT/JP2022/023683, filed on Jun. 13, 2022.

(30) Foreign Application Priority Data

Aug. 10, 2021 (JP) ................................ 2021-130936

(51) Int. Cl.
*A61M 5/142* (2006.01)

(52) U.S. Cl.
CPC ......... *A61M 5/142* (2013.01); *A61M 2207/10* (2013.01)

(58) Field of Classification Search
CPC .... A61M 5/142; A61M 5/14244; A61M 5/14; A61M 5/152; A61M 2207/10; A61J 1/05
See application file for complete search history.

(56) References Cited

U.S. PATENT DOCUMENTS 3,653,377 A * 4/1972 Rebold ............... A61M 3/0258 604/153
6,530,900 B1 * 3/2003 Daily .................... A61M 5/155 604/141
2010/0179473 A1 * 7/2010 Genosar ........... A61M 5/14248 604/82

FOREIGN PATENT DOCUMENTS

JP 3048087 U 5/1998
JP 2015-167709 A 9/2015
WO WO-2021/106425 A1 6/2021

OTHER PUBLICATIONS

International Search Report and Written Opinion of the International Searching Authority issued in the corresponding International Patent Application No. PCT/JP2022/023683, dated Jul. 12, 2022.

(Continued)

*Primary Examiner* — Laura A Bouchelle
*Assistant Examiner* — Sarah Dympna Grasmeder
(74) *Attorney, Agent, or Firm* — Foley & Lardner LLP

(57) ABSTRACT

An infusion cartridge includes: a case provided with a recess; and a film structure that has flexibility, covers an opening of the recess, and, together with the recess, defines a storage space configured to store an infusion solution. The case includes an opening end that defines the opening of the recess, the opening end including: a first side surface facing inside of the recess, a second side surface located on a side opposite to the first side surface, and an end surface connecting the first side surface and the second side surface. The film structure includes: a fixing portion that covers the end surface and is fixed to the end surface, and a cover portion that covers the second side surface and is not fixed to the second side surface.

9 Claims, 11 Drawing Sheets

(56) References Cited

OTHER PUBLICATIONS

Written Opinion of the International Searching Authority issued in the corresponding International Patent Application No. PCT/JP2022/023683, dated Jul. 12, 2022 with English translation.

* cited by examiner

INFUSION CARTRIDGE, INFUSION PUMP, AND METHOD FOR MANUFACTURING INFUSION CARTRIDGE

CROSS-REFERENCE TO RELATED APPLICATIONS

This is a bypass continuation of PCT Application No. PCT/JP2022/023683, filed on Jun. 13, 2022, which claims priority to Japanese Application No. JP2021-130936, filed on Aug. 10, 2021. The entire contents of these applications are incorporated herein by reference.

BACKGROUND

This disclosure relates to an infusion cartridge, an infusion pump, and a method for manufacturing an infusion cartridge.

In the related art, there is known an infusion pump that feeds an infusion solution such as liquid medicine. Patent Literature 1 discloses an example of this type of infusion Japanese Patent Publication No. 2015-167709 A ("Patent Literature 1") discloses a liquid transport device including a tank that pools a liquid, a pump unit that compresses a tube to transport the liquid in the tank to a living body, and an injection unit that injects the liquid transported by the pump unit into the living body.

In the example disclosed in Patent Literature 1, a reservoir as the tank is disposed in a cartridge. A recess is formed in a cartridge body disclosed in Patent Literature 1, and a film is fusion bonded around the recess. The reservoir as the tank includes the recess and the film. The liquid is pooled between the recess and the film.

SUMMARY

In Patent Literature 1, the reservoir is formed by fusion bonding the film, or a film structure, around the recess but there is still room for improvement in protectiveness of the fusion bonded part.

An object of this disclosure is to provide an infusion cartridge, an infusion pump, and a method for manufacturing an infusion cartridge capable of enhancing protectiveness of mutually fixed portions of a case and a film structure defining a storage space.

An infusion cartridge according to a first aspect of this disclosure is an infusion cartridge that defines a storage space capable of storing an infusion solution, the infusion cartridge including: a case provided with a recess; and a film structure that has flexibility, covers an opening of the recess, and defines the storage space together with the recess, in which the case includes an opening end that defines the opening of the recess, the opening end includes a first side surface facing inside of the recess, a second side surface located on a side opposite to the first side surface, and an end surface connecting the first side surface and the second side surface, and the film structure includes a fixing portion that covers the end surface and is fixed to the end surface and a cover portion that covers the second side surface and is not fixed to the second side surface.

As an embodiment of this disclosure, the film structure includes a reinforcing portion that protrudes from the cover portion in an out-of-plane direction of the second side surface.

As an embodiment of this disclosure, the film structure includes a film body that is located on a side closer to the recess than the fixing portion and is deformed when the infusion solution is stored in the storage space, and the film body enters the recess from the opening of the recess toward a bottom surface in a state in which the infusion solution is not stored in the storage space.

As an embodiment of this disclosure, the recess of the case has a side surface including the first side surface of the opening end, and the film body covers a predetermined region including the first side surface of the side surface of the recess in a state in which the infusion solution is not stored in the storage space.

As an embodiment of this disclosure, the predetermined region has a length in a depth direction of the recess accounting for 70% to 98% of a maximum depth of the recess.

As an embodiment of this disclosure, the case includes a case body provided with the recess and a lid rotatably attached to the case body via a hinge portion, the lid being rotatable relative to the case body by the hinge portion to open and close the case body between a state of uncovering the film structure and a state of covering the film structure, and the hinge portion being disposed closer to a bottom surface of the recess in a depth direction of the recess than the cover portion of the film structure.

As an embodiment of this disclosure, the case is provided with a ventilation port through which a gas in the storage space is discharged.

An infusion pump as a second aspect of this disclosure includes the infusion cartridge and a pump body to which the infusion cartridge is attachable.

A method for manufacturing an infusion cartridge as a third aspect of this disclosure is a method for manufacturing an infusion cartridge that defines a storage space capable of storing an infusion solution, the method including the step of covering an opening of a recess of a case with a film structure having flexibility to define the storage space between the recess of the case and the film structure, in which the case includes an opening end that defines the opening of the recess, the opening end includes a first side surface facing inside of the recess, a second side surface facing a side opposite to the inside of the recess, and an end surface connecting the first side surface and the second side surface, and in the step, the film structure is fixed to the end surface while being positioned to cover the end surface and the second side surface in the opening end of the case.

According to this disclosure, it is possible to provide an infusion cartridge, an infusion pump, and a method for manufacturing an infusion cartridge capable of enhancing protectiveness of mutually fixed portions of a case and a film structure defining a storage space.

DETAILED DESCRIPTION

Figure 1:
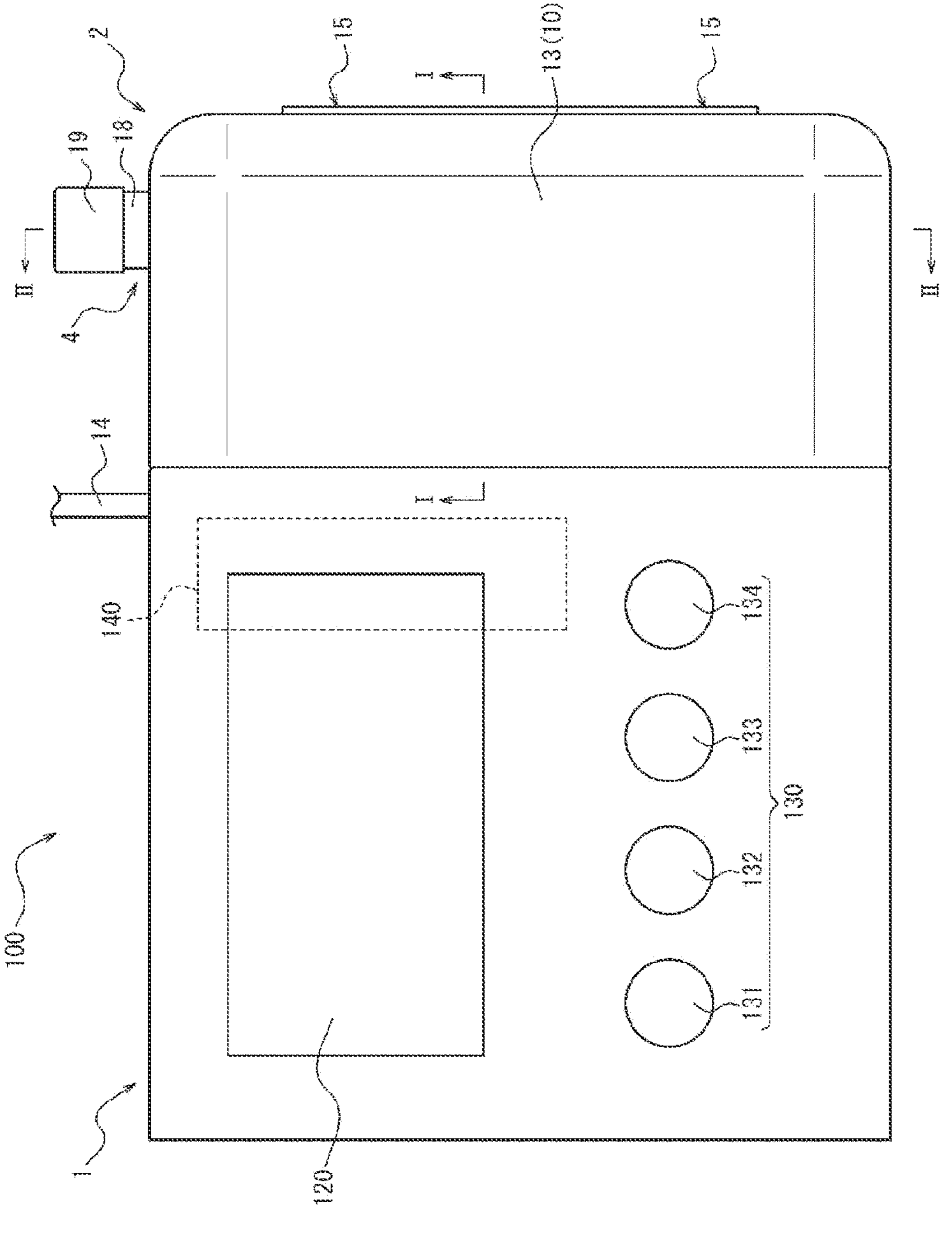
FIG. 1 is a front view of an infusion pump as an embodiment of this disclosure including an infusion cartridge as an embodiment of this disclosure.

Hereinafter, an infusion cartridge, an infusion pump, and a method for manufacturing an infusion cartridge according to embodiments of the disclosure will be illustrated with reference to the drawings. In the drawings, the same components are denoted by the same reference numerals.

FIG. 1 is a front view of an infusion pump 100 as an embodiment of the infusion pump according to this disclosure. As illustrated in FIG. 1, the infusion pump 100 includes a pump body 1 and an infusion cartridge 2 as an embodiment of the infusion cartridge according to this disclosure. The infusion pump 100 illustrated in FIG. 1 is available as, for example, a patient controlled analgesia (PCA) pump but is not particularly limited thereto. In the infusion pump 100 of this embodiment, the pump body 1 is reusable by replacing the disposable infusion cartridge 2.

Pump Body 1

As illustrated in FIG. 1, the pump body 1 has a front surface provided with a display unit 120 that shows various types of information, and an operation unit 130 in which operating switches are arranged. The display unit 120 shows, for example, a liquid feed rate and a cumulative dose. Alternatively, the display unit 120 may be a liquid crystal screen with a touch panel for setting a liquid feed rate and the like. The operating switches of the operation unit 130 illustrated in FIG. 1 include a fast delivery switch 131, a start switch 132, a stop switch 133, and a power supply switch 134. While the fast delivery switch 131 is pushed, a liquid is fed at a liquid feed rate higher than a set liquid feed rate (mL/h). When the start switch 132 is pushed, the liquid feeding starts. When the stop switch 133 is pushed, the liquid feeding is forced to stop. When the power supply switch 134 is pushed, the power supply of the pump body 1 is switched between ON and OFF. It should be noted that the operation unit 130 may include another operating switch. The display unit 120 and the operation unit 130 make it possible to feed an infusion solution into a living body of a patient or the like while controlling an amount of liquid fed.

The pump body 1 also includes a liquid feeding unit 140 that sandwiches a tube portion 14 of the infusion cartridge 2 together with a tube holder 30 (to be described later, see FIG. 2) of the infusion cartridge 2 that is to be attached to the pump body 1. The liquid feeding unit 140 feeds the infusion solution inside the tube portion 14 from the upstream side to the downstream side of a flow path. The liquid feeding unit 140 of this embodiment includes a plurality of fingers and a drive unit that drives the fingers. The plurality of fingers is arranged on a side surface of the pump body 1 facing the tube holder 30 (to be described later, see FIG. 2) located on a side surface of the infusion cartridge 2. The plurality of fingers is arranged along an extending direction of the tube portion 14. Each finger is driven by the drive unit to reciprocate in a direction facing the tube holder 30 (to be described later, see FIG. 2) of the infusion cartridge 2. When each finger moves to approach the infusion cartridge 2, the tube portion 14 is sandwiched between each finger and the tube holder 30. Accordingly, the tube portion 14 is compressed and closed. The drive unit sequentially drives the fingers from the upstream side to the downstream side of the flow path in the extending direction of the tube portion 14. The drive unit may include, for example, an electric motor. With this configuration, the tube portion 14 is compressed and closed sequentially from the upstream side to the downstream side of the flow path and moves peristaltically. Accordingly, the infusion solution inside the tube portion 14 is fed from the upstream side to the downstream side of the flow path.

The pump body 1 is not limited to the configuration of this embodiment. In addition to the aforementioned parts, the pump body 1 may include, for example, a notification unit such as bubble detection sensor and occlusion sensor. As described above, the liquid feeding unit 140 of the pump body 1 of this embodiment compresses the tube portion 14 by the plurality of fingers, but the liquid feeding unit 140 may include a compressing unit different from the fingers as long as it enables feeding of the infusion solution inside the tube portion 14.

Infusion Cartridge 2

Figure 2:
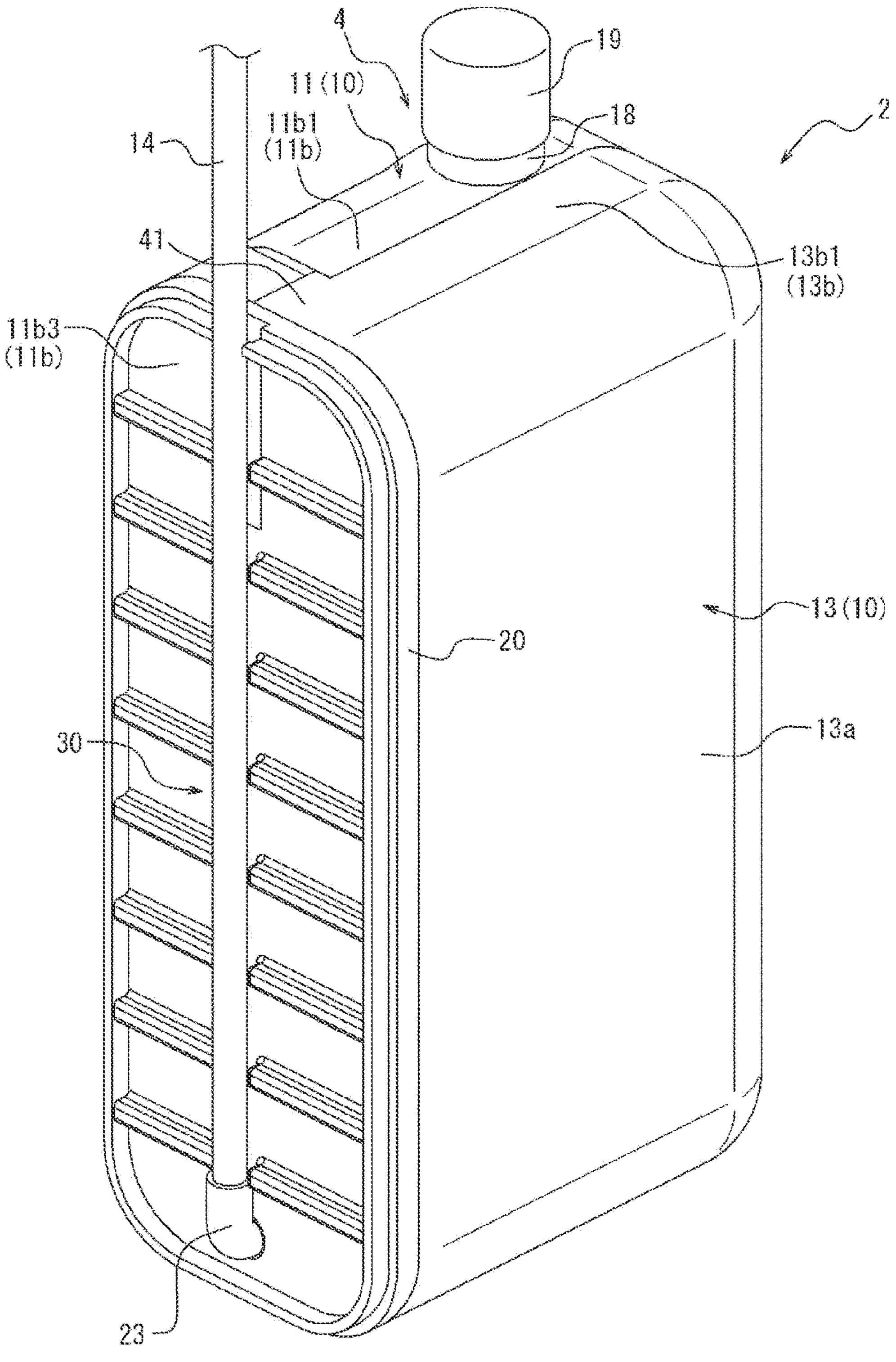
FIG. 2 is a perspective view of the infusion cartridge illustrated in FIG. 1 in isolation.
Figure 3:
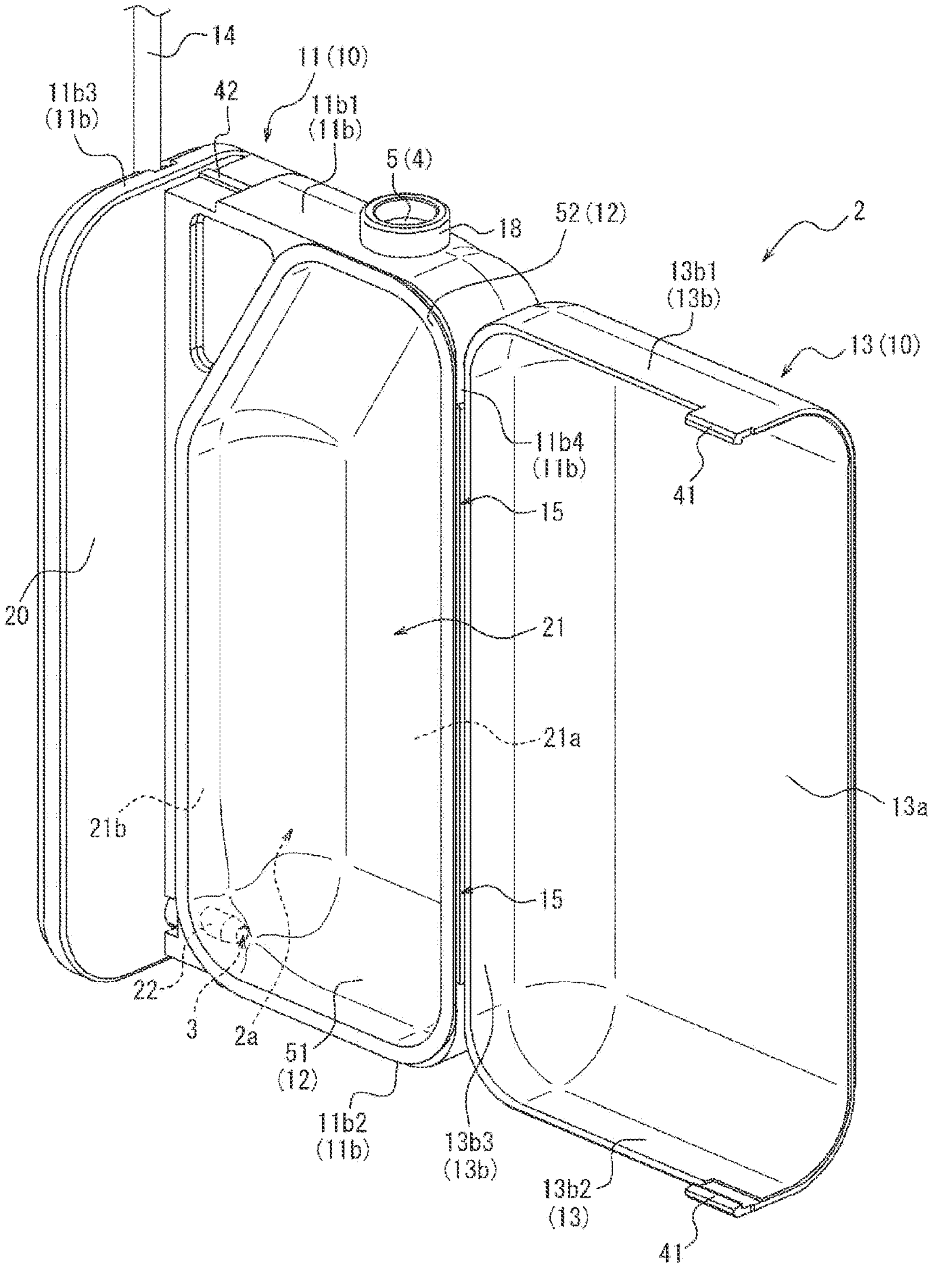
FIG. 3 is a perspective view illustrating a state in which a lid of the infusion cartridge illustrated in FIG. 2 not filled with an infusion solution is opened to expose the interior of a case body.
Figure 4:
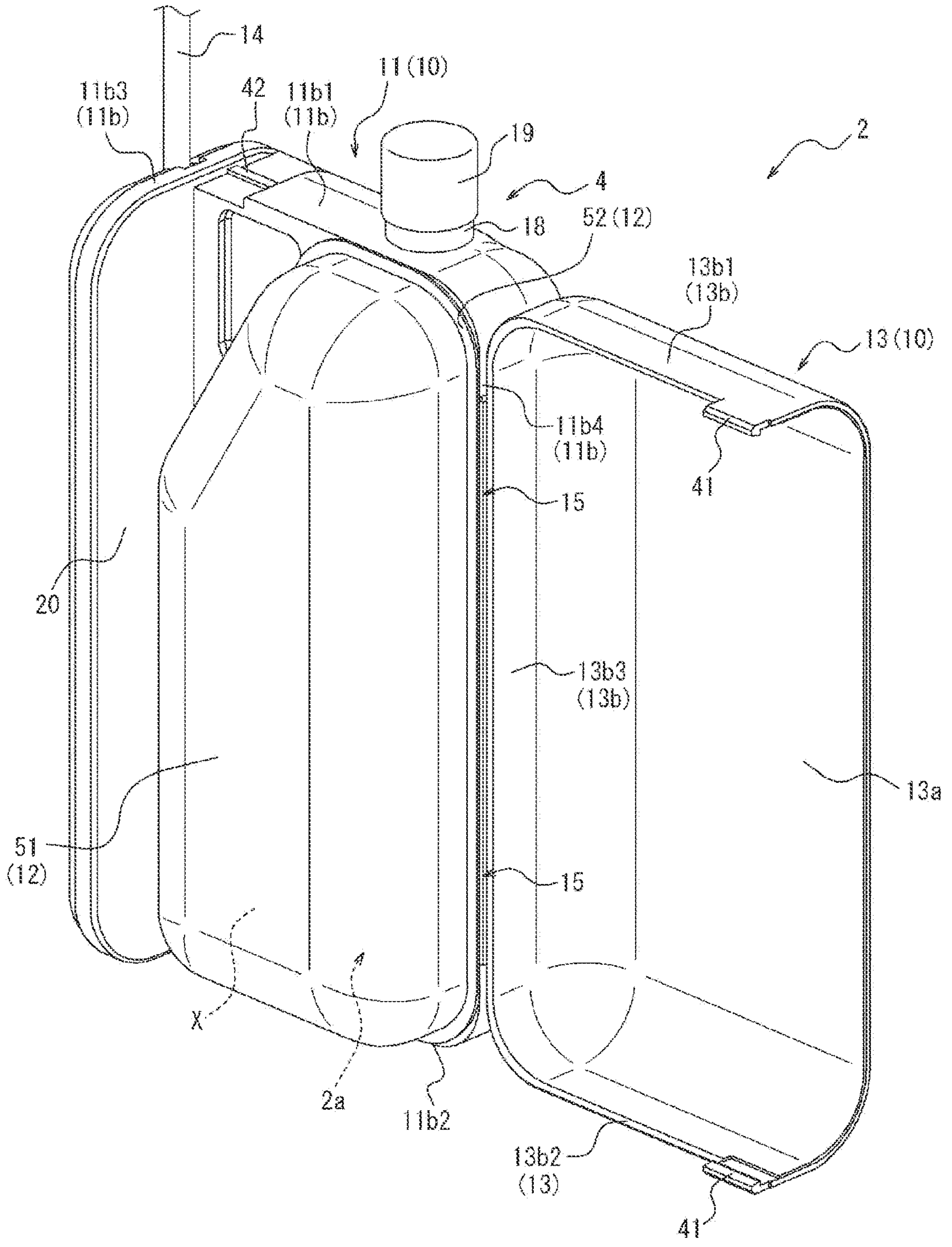
FIG. 4 is a perspective view illustrating a state in which the lid of the infusion cartridge illustrated in FIG. 2 filled with the infusion solution is opened to expose the interior of the case body.
Figure 5:
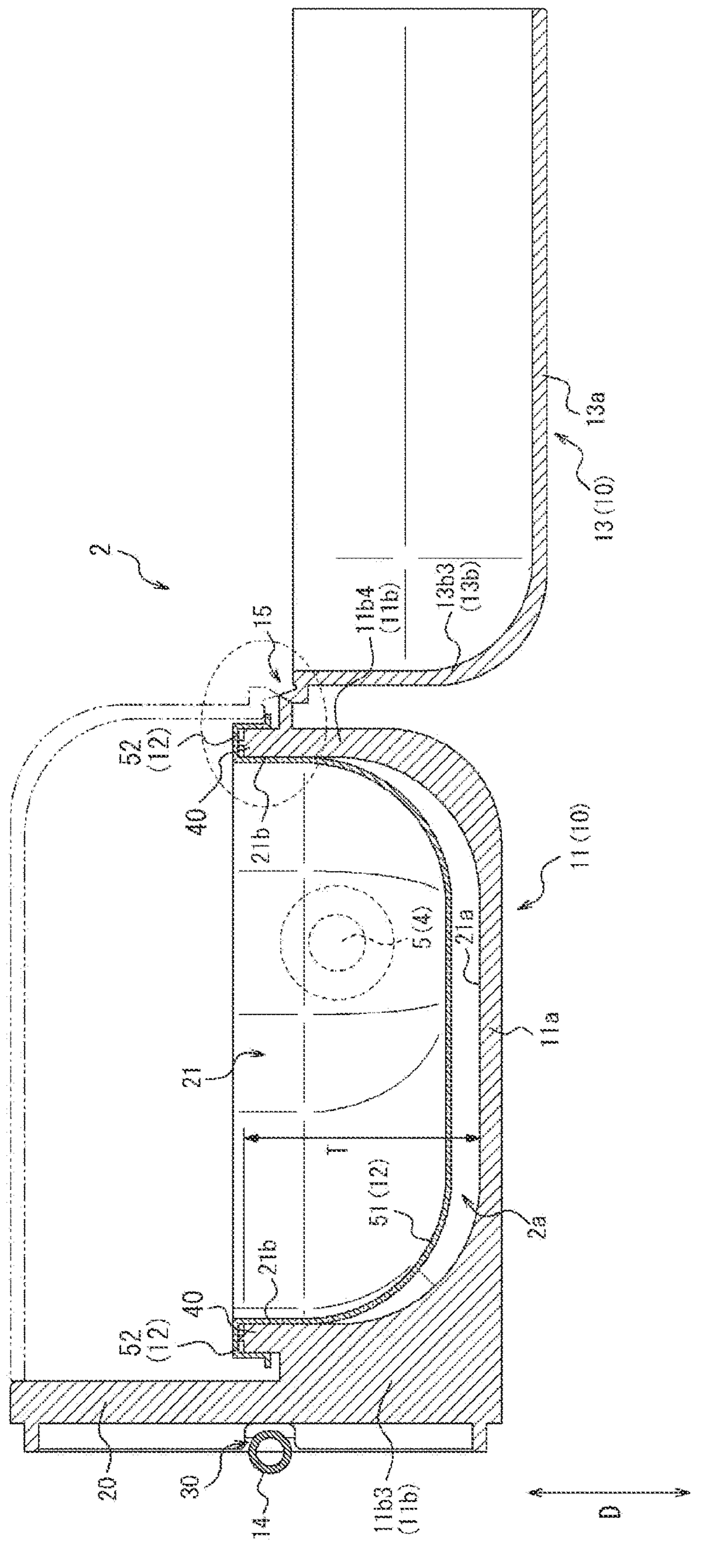
FIG. 5 is a cross-sectional view of the infusion cartridge taken along line I-I in FIG. 1, illustrating a state in which the infusion cartridge is not filled with the infusion solution.
Figure 6:
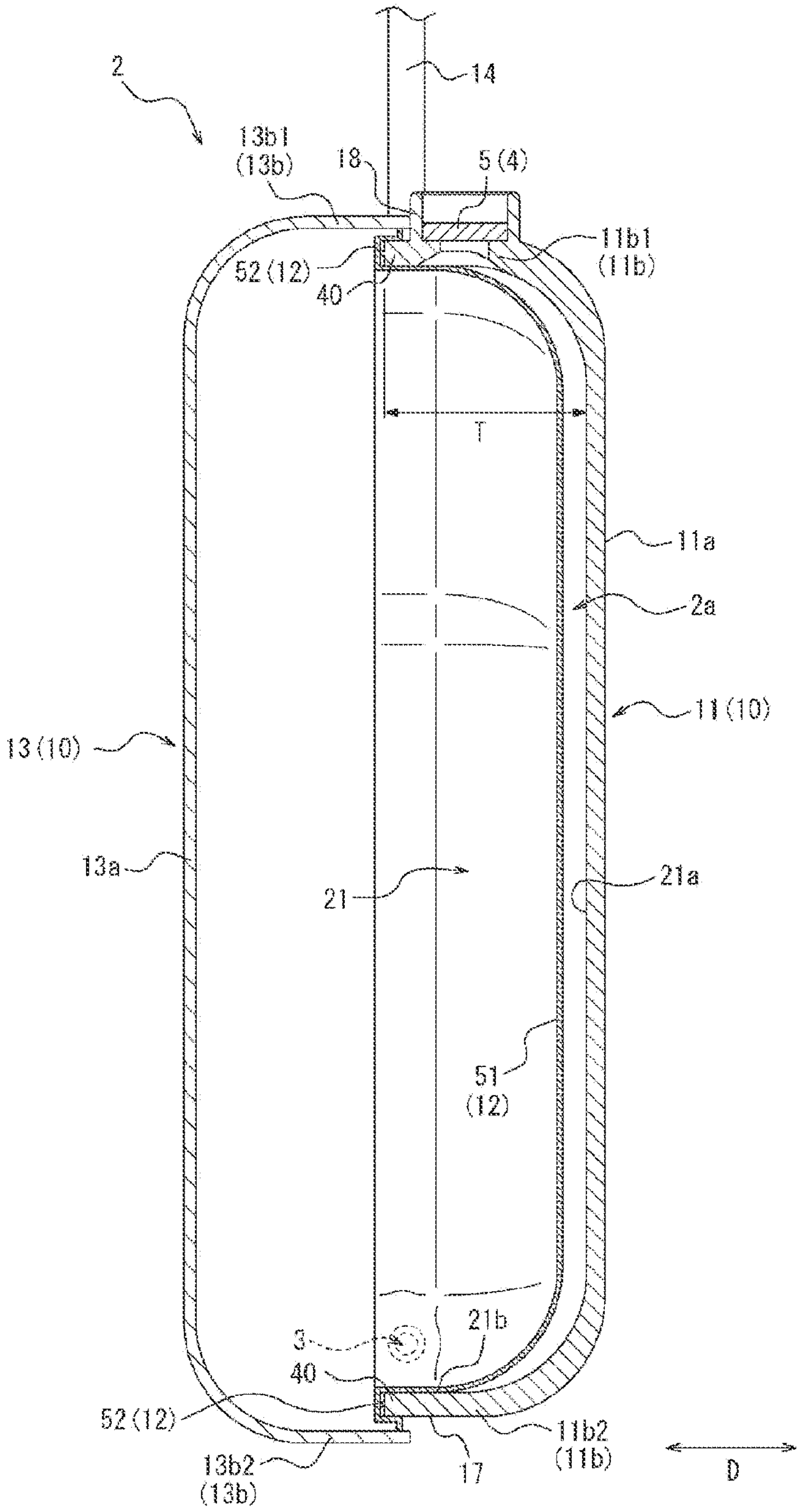
FIG. 6 is a cross-sectional view of the infusion cartridge taken along line II-II in FIG. 1, illustrating the state in which the infusion cartridge is not filled with the infusion solution.

FIG. 2 is a perspective view of the infusion cartridge 2 in isolation. FIGS. 3 and 4 are perspective views each illustrating a state in which a lid 13 of the infusion cartridge 2 illustrated in FIG. 2 is opened to expose the interior of a case body 11. FIG. 3 illustrates a state in which the infusion cartridge 2 is not filled with an infusion solution X. FIG. 4 illustrates a state in which the infusion cartridge 2 is filled with the infusion solution X. FIGS. 5 and 6 are cross-sectional views illustrating the infusion cartridge 2 taken along different lines. Specifically, FIG. 5 is a cross-sectional view taken along line I-I in FIG. 1.

FIG. 6 is a cross-sectional view taken along line II-II in FIG. 1. FIGS. 5 and 6 illustrate a state in which the infusion cartridge 2 is not filled with the infusion solution X.

Figure 7:
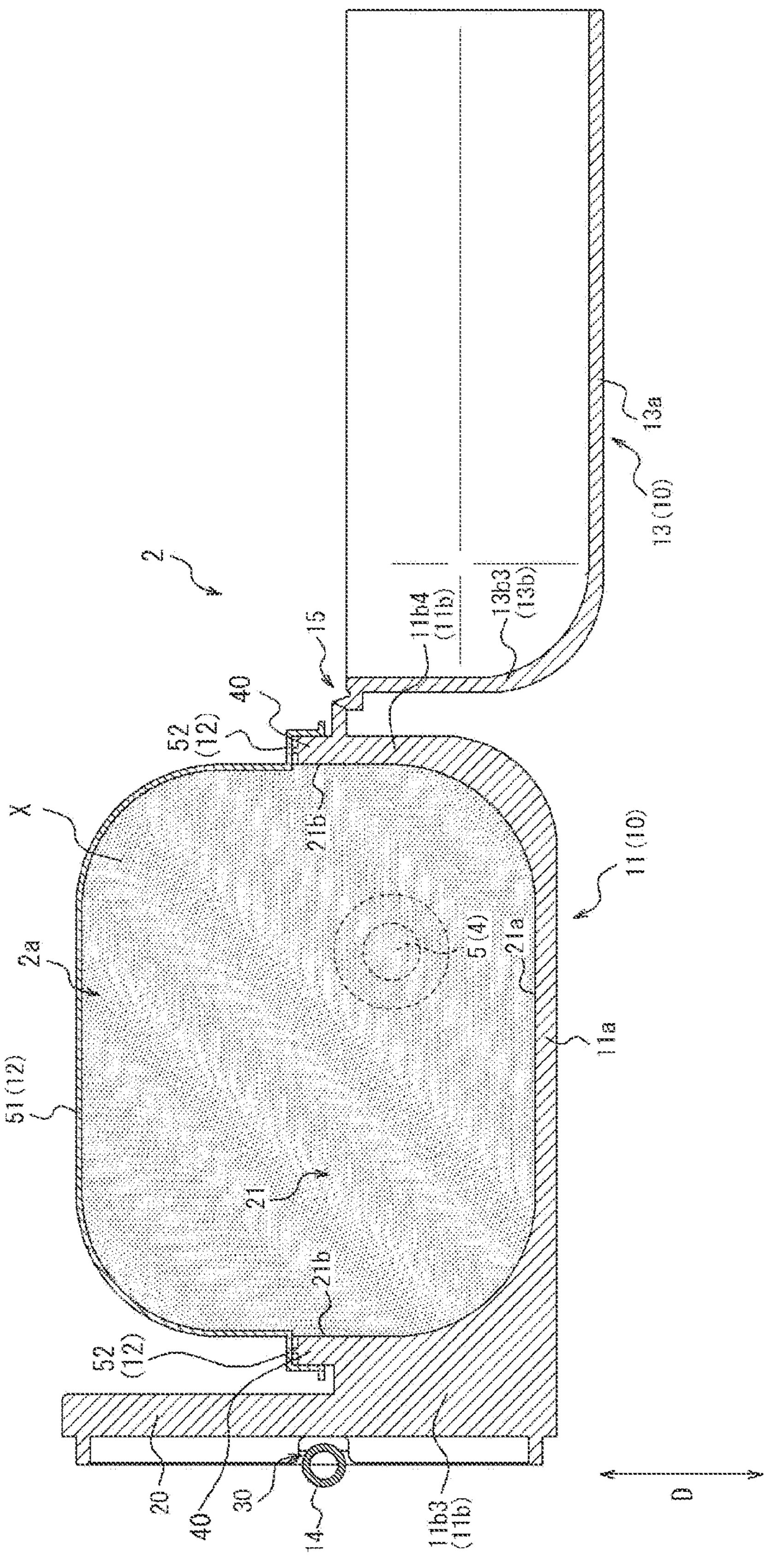
FIG. 7 is a cross-sectional view of the infusion cartridge taken along the same line as FIG. 5, illustrating a state in which the infusion cartridge is filled with the infusion solution.
Figure 8:
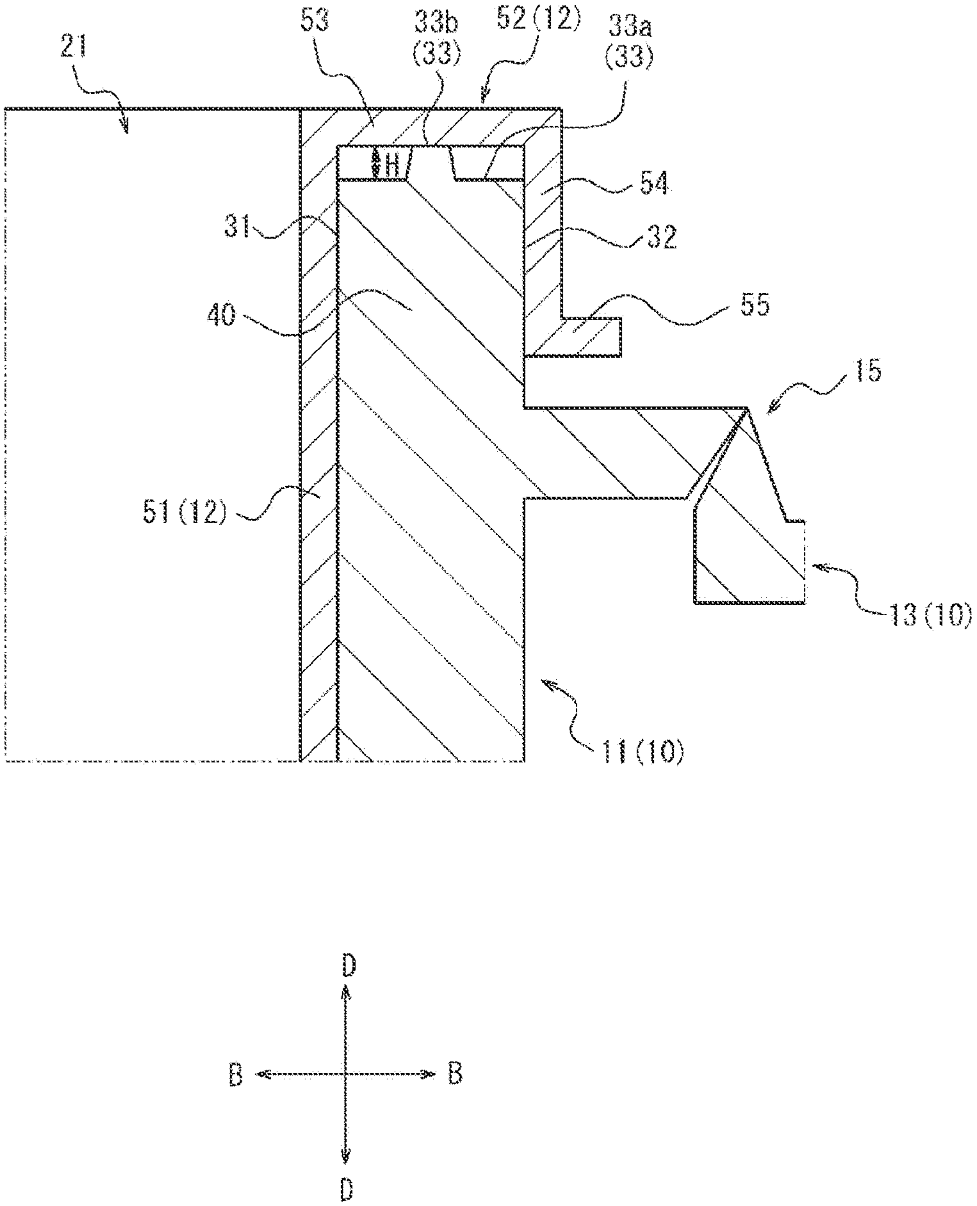
FIG. 8 is an enlarged view in which a part of FIG. 5 is enlarged.

FIG. 7 is a cross-section taken along the same line as FIG. 5, illustrating a state in which the infusion cartridge 2 is filled with the infusion solution X. FIGS. 5 and 7 illustrate states where the lid 13 is opened to expose the interior of the case body 11. In FIG. 5, dash-dot-dot lines indicate a state in which the lid 13 is closed to cover the interior of the case body 11. FIG. 6 illustrate the state in which the lid 13 is closed to cover the interior of the case body 11. FIG. 8 is an enlarged view in which a part of FIG. 5 is enlarged.

As illustrated in FIGS. 3 to 7, the infusion cartridge 2 defines a storage space 2*a* that stores the infusion solution X such as liquid medicine. In addition, as illustrated in FIGS. 3 and 4, the infusion cartridge 2 includes a case 10 and a film structure 12.

As illustrated in FIGS. 5 to 7, a recess 21 is formed in the case 10. As illustrated in FIGS. 5 to 7, the recess 21 of this embodiment includes a planar bottom surface 21*a* and a side surface 21*b* rising directly from the outer edge of the bottom surface 21*a*. An opening end 40 that defines an opening of the recess 21 includes ends of the side surface 21*b* that are on the opposite side of the bottom surface 21*a*, that is, edges of the recess 21. The recess 21 of this embodiment has such a shape but is not particularly limited thereto. The bottom surface 21*a* and the side surface 21*b* of the recess 21 may be either planar or curved. However, the bottom surface 21*a* and the side surface 21*b* are preferably curved and smoothly continuous with each other to prevent the retention of bubbles.

The film structure 12 has flexibility. As illustrated in FIGS. 3 to 7, the film structure 12 covers the opening of the recess 21 of the case 10 and defines the storage space 2*a* together with the recess 21. Furthermore, the film structure 12 is fixed to the opening end 40 of the case 10. The case 10 and the film structure 12 of this embodiment are bonded and fixed to each other by, for example, welding such as ultrasonic fusion welding, but a method for fixing the members is not particularly limited. Other fixing methods may be employed as long as a gap between the case 10 and the film structure 12 is sealed in a liquid-tight and airtight manner. Therefore, as long as the gap between the case 10 and the film structure 12 is sealed liquid-tightly and airtightly, a separate member may be or not necessarily be interposed between the case 10 and the film structure 12.

More specifically, as illustrated in FIGS. 5 to 7, the film structure 12 is fixed to the case 10 to cover a surface of the opening end 40 of the case 10 that is opposite to a surface on the side closer to the recess 21. Details of this configuration will be described later (see FIG. 8).

The case 10 has shape stability and is not deformed even by an internal pressure of the infusion solution X stored in the storage space 2*a*. In particular, a part of the case 10 that defines the storage space 2*a* together with the film structure 12 is less likely to be deformed than the film structure 12. Examples of a material for the case 10 include various resin materials, that is, polyolefins such as polyethylene, polypropylene, and ethylene-propylene copolymers; ethylene-vinyl acetate copolymers (EVA); polyvinyl chloride; polyvinylidene chloride; polystyrene; polyamides; polyimides; polyamide-imides; polycarbonates; poly-(4-methylpentene-1); ionomers; acrylic resins; polymethyl methacrylate; acrylonitrile-butadiene-styrene copolymers (ABS resin); acrylonitrile-styrene copolymers (AS resin); butadiene-styrene copolymers; polyesters such as polyethylene terephthalate (PET), polybutylene terephthalate (PBT), and polycyclohexane terephthalate (PCT); polyethers; polyetherketone (PEK); polyetheretherketone (PEEK); polyetherimides; polyacetals (POM); polyphenylene oxides; modified polyphenylene oxides; polysulfones; polyether sulfones; polyphenylene sulfides; polyarylates; aromatic polyesters (liquid crystal polymers); polytetrafluoroethylene, polyvinylidene fluoride, and other fluorine-based resins. The case 10 is molded using, for example, the aforementioned resin materials.

The film structure 12 is deformed by the internal pressure of the infusion solution X stored in the storage space 2*a*. The film structure 12 is thinner than the case 10 at any position of the part that defines the storage space 2*a*. The volume of the storage space 2*a* varies with deformation of the film structure 12. In addition to the materials used for forming the case 10, examples of a material for the film structure 12 include various rubber materials such as natural rubber, isoprene rubber, butadiene rubber, styrene-butadiene rubber, nitrile rubber, chloroprene rubber, butyl rubber, acrylic rubber, ethylene-propylene rubber, Hydrin rubber, urethane rubber, silicone rubber, and fluororubber and various thermoplastic elastomers such as styrene-based, polyolefin-based, polyvinyl chloride-based, polyurethane-based, polyester-based, polyamide-based, polybutadiene-based, trans-polyisoprene-based, fluorine-based, and chlorinated polyethylene-based elastomers, but preferred examples are polyolefins such as polyethylene, polypropylene, and ethylene-propylene copolymers. The film structure 12 may have an outside diameter of, for example, 0.2 mm to 0.5 mm. As in this embodiment, in a case where the case 10 and the film structure 12 are fixed to each other by welding, at least a part of the case 10 to be welded to the film structure 12 and the film structure 12 preferably include the same resin material such as polypropylene.

As illustrated in FIGS. 3 and 6, a filling port 3 and a ventilation port 4 are formed on an inner wall that defines the storage space 2*a*. Through the filling port 3, the infusion solution X is filled into the storage space 2*a* from the outside. Through the ventilation port 4, a gas inside the storage space 2*a* is discharged.

As described above, the storage space 2*a* of the infusion cartridge 2 is defined by the recess 21 of the case 10 and the film structure 12 covering the opening of the recess 21. With such a configuration, the inner wall of the recess 21 of the case 10 that defines the storage space 2*a* is not deformed by an internal pressure of the infusion solution X in the storage space 2*a*. Accordingly, it is possible to prevent deformation of the inner wall defining the storage space 2*a*, thereby preventing wrinkles or the like where bubbles easily accumulate. Therefore, bubbles are less likely to accumulate in the storage space 2*a*. The filling port 3 and the ventilation port 4 are formed in the inner wall that defines the storage space 2*a* of this embodiment. Separating the ventilation port 4 and the filling port 3 makes it possible to discharge the gas in the storage space 2*a* through the ventilation port 4 while filling the storage space 2*a* with the infusion solution X through the filling port 3. Accordingly, it is possible to easily discharge the gas from the storage space 2*a* as compared with a configuration including the filling port 3 and without the ventilation port 4 as a separate member.

As illustrated in FIG. 6, the ventilation port 4 of this embodiment includes a ventilation filter 5. Furthermore, as the ventilation filter 5, it is preferable to use a filter with a hydrophobized surface or a hydrophobic film (hydrophobizing film). Examples of a constituent material of the hydrophobic film include polytetrafluoroethylene (PTFE), copolymers of tetrafluoroethylene and hexafluoropropylene (FEP), copolymers of tetrafluoroethylene and perfluoroalkyl vinyl ether (PFA), and polyvinylidene fluoride (PVDF). The ventilation filter 5 is preferably obtained, for example, by making these materials into porous materials by stretching, micro-phase separation, electron beam etching, and sintering methods or with argon plasma particles. In addition, a method of hydrophobization is not particularly limited. For example, the surface of the ventilation filter 5 may be coated with a hydrophobic constituent material. Furthermore, the ventilation filter 5 is not limited to the above configuration as long as it allows gas permeation and does not allow liquid permeation and may include other materials such as hydrophilic materials. Such a hydrophobic ventilation filter 5 enables the gas in the storage space 2*a* to be discharged and prevents the infusion solution X in the storage space 2*a* from leaking out.

The filling port 3 of this embodiment is used not only for filling of the infusion solution X into the storage space 2*a* from the outside but also for feeding of the infusion solution X to a living body from the storage space 2*a*. In other words, the filling port 3 of this embodiment also serves as a feed port for feeding the infusion solution X to a living body. However, a feed port different from the filling port 3 may be disposed on the inner wall that defines the storage space 2*a*.

Hereinafter, further details of the infusion cartridge 2 of this embodiment will be described.

As illustrated in FIGS. 3 to 7, the infusion cartridge 2 of this embodiment includes the tube portion 14 in addition to the case 10 and the film structure 12. The case 10 of this embodiment includes the case body 11 and the lid 13. Further details of each part in the infusion cartridge 2 of this embodiment will now be described.

The case body 11 of the case 10 is provided with the recess 21. The case body 11 of this embodiment has shape stability and is not deformed even by an internal pressure of the infusion solution X stored in the storage space 2*a*. In other words, a part of the case body 11 constituting the inner surface of the recess 21 is larger in flexural rigidity than the film structure 12. Accordingly, the film structure 12 is deformed more preferentially than the case body 11 by an internal pressure of the infusion solution X stored in the storage space 2*a*. The case body 11 of the case 10 of this embodiment includes a tabular bottom plate portion 11*a* and a side plate portion 11*b* rising from outer edges of the bottom plate portion 11*a* in a thickness direction of the bottom plate portion 11*a*. The bottom plate portion 11*a* has a substantially quadrangular outline in a plan view as viewed in the thickness direction. The side plate portion 11*b* rises from four outer edges of the bottom plate portion 11*a* that extend substantially linearly. The recess 21 of the case body 11 of this embodiment is defined by the bottom plate portion 11*a* and the side plate portion 11*b*. More specifically, the bottom surface 21*a* of the recess 21 of this embodiment includes the inner surface of the bottom plate portion 11*a*. In addition, the side surface 21*b* of the recess 21 of this embodiment includes the inner surface of the side plate portion 11*b*.

In this embodiment, the filling port 3 is formed not in the film structure 12 but in the recess 21 of the case body 11. With this configuration, the position of the filling port 3 does not change according to the presence or absence of the infusion solution X in the storage space 2*a* nor the amount of the infusion solution X. Therefore, it is possible to enhance position stability of the tube portion 14 (to be described) that communicates a fluid to the filling port 3.

In this embodiment, the ventilation port 4 is formed in the recess 21 of the case 10. If the ventilation port 4 is formed in the film structure 12, the ventilation port 4 is probably occluded by the deformation of the film structure 12. In contrast, forming the ventilation port 4 in the recess 21 of the case 10 makes it difficult to occlude the ventilation port 4, which promotes discharge of the gas.

In this embodiment, the side plate portion 11*b* of the case body 11 of the case 10 includes a first plate portion 11*b*1 provided with the ventilation port 4. The side plate portion 11*b* of the case body 11 of this embodiment also includes a second plate portion 11*b*2 facing the first plate portion 11*b*1. Furthermore, the side plate portion 11*b* of the case body 11 of this embodiment includes a third plate portion 11*b*3 continuous with one end of the first plate portion 11*b*1 and one end of the second plate portion 11*b*2. Still further, the side plate portion 11*b* of the case body 11 of this embodiment includes a fourth plate portion 11*b*4 that is continuous with the other end of the first plate portion 11*b*1 and the other end of the second plate portion 11*b*2 and faces the third plate portion 11*b*3. The filling port 3 is disposed in the third plate portion 11*b*3 of the side plate portion 11*b*.

The first plate portion 11*b*1 and the second plate portion 11*b*2 of this embodiment are provided with catches 42 that hook locking claws 41 of the lid 13 (to be described) when the lid 13 is closed.

In this embodiment, a part on the inner surface side of the third plate portion 11*b*3 rises up to the same height as top end surfaces of the first plate portion 11*b*1, the second plate portion 11*b*2, and the fourth plate portion 11*b*4. On the other hand, the remaining part on the outer surface side of the third plate portion 11*b*3 of this embodiment further extends from the top end surfaces of the first plate portion 11*b*1, the second plate portion 11*b*2, and the fourth plate portion 11*b*4. This extended part will hereinafter be referred to as "extended portion 20." Therefore, in the case body 11, the opening end 40 of the case 10 of this embodiment includes top ends of the first plate portion 11*b*1, the second plate portion 11*b*2, and the fourth plate portion 11*b*4 and a top end of a part of the third plate portion 11*b*3 on the inner surface side.

As illustrated in FIG. 8, the opening end 40 of the case 10 includes a first side surface 31, a second side surface 32, and an end surface 33. The first side surface 31 faces the inside of the recess 21 near the opening of the recess 21. The second side surface 32 is located on the side opposite to the first side surface 31. The end surface 33 connects the first side surface 31 and the second side surface 32. The end surface 33 extends endlessly. That is to say, the inner edge of the end surface 33 closer to the recess 21 is continuous with the first side surface 31. The outer edge of the end surface 33 on the side opposite to the recess 21 is continuous with the second side surface 32. Details of a fixing structure for the opening end 40 of the case 10 and the film structure 12 will be described later.

The tube holder 30 that receives the tube portion 14 and sandwiches the tube portion 14 together with the pump body 1 is formed on the outer surface of the third plate portion 11*b*3.

The lid 13 (to be described) is rotatably attached to the fourth plate portion 11*b*4 by a hinge portion 15.

As illustrated in FIG. 3, a cylindrical portion 22 protruding toward the storage space 2*a* is formed on the inner surface of the recess 21. The filling port 3 of this embodiment includes a distal opening of the cylindrical portion 22. More specifically, in this embodiment, the cylindrical portion 22 is formed on the inner surface of the third plate portion 11*b*3. The filling port 3 including the distal opening of the cylindrical portion 22 as described above makes it difficult for bubbles adhering to the inner wall defining the storage space 2*a* to enter the filling port 3 as compared with a configuration without the cylindrical portion 22. In other words, even when the storage space 2*a* contains bubbles, the bubbles hardly reach the distal opening of the cylindrical portion 22, which prevents the bubbles from being discharged through the filling port 3.

The proximal side of the cylindrical portion 22 extends to the outside of the storage space 2*a*. The tube portion 14 (to be described) is connected to the proximal side of the cylindrical portion 22 via an L-shaped connecting tube portion 23 illustrated in FIG. 2. Accordingly, a hollow portion of the tube portion 14 communicates with the storage space 2*a* through the filling port 3. However, the connection between the tube portion 14 and the filling port 3 is not limited to the configuration of this embodiment.

As described above, the ventilation port 4 of this embodiment includes the ventilation filter 5. More specifically, as illustrated in FIGS. 3 and 4, the cylindrical portion 18 protruding outward is formed on the outer surface of the first plate portion **11*b*1 of the side plate portion 11*b* of the case body 11. The cylindrical portion 18 defines a communication hole that allows the outside and the storage space 2*a* to communicate with each other. The ventilation filter 5 is disposed in the communication hole. As illustrated in FIGS. 1 and 2, after the storage space 2*a* is filled with the infusion solution X, a cap 19 is attached to the cylindrical portion 18. The cap 19 closes the communication hole of the cylindrical portion 18. Such a configuration enables protection of the ventilation filter 5 and also prevents a gas from flowing into the storage space 2*a* from the outside through the ventilation port 4. The cap 19 is not particularly limited in configuration as long as it closes the cylindrical portion 18 by being attached to the cylindrical portion 18. However, the cap 19 preferably has a permanently set structure that is unremovable once attached to the cylindrical portion 18 so as not to break the ventilation filter 5 or not to allow a gas to flow through the ventilation port 4 after the storage space 2*a*** is once filled with the infusion solution X.

The film structure 12 of this embodiment includes a film body 51 and a peripheral edge 52. The film body 51 covers the opening of the recess 21 in the case body 11 of the case 10 and defines the storage space **2*a* together with the recess 21. The peripheral edge 52 is the outer edge of the film structure 12 surrounding the periphery of the film body 51. The peripheral edge 52 is fixed to the opening end 40 of the case 10**.

As illustrated in FIGS. 3 to 8, the film body 51 is deformable. As illustrated in FIGS. 3, 5, and 6, in a state in which the infusion solution X is not stored in the storage space **2*a*, the film body 51 of this embodiment enters the recess 21 from the opening of the recess 21 toward the bottom surface 21*a*. In other words, the film body 51 of this embodiment is recessed along the inner surface of the recess 21 in the state in which the infusion solution X is not stored in the storage space 2*a*. In contrast, as illustrated in FIGS. 4 and 7, when the storage space 2*a* is filled with the infusion solution X, the film body 51 is pushed and inflated by the filled infusion solution X, thereby causing the film body 51 to deform and protrude from the opening of the recess 21. In a case where bubbles remain in the filled infusion solution X, the other end of the tube portion 14 is closed and the protruded film body 51 is pushed from the outside, thereby discharging the bubbles from the ventilation port 4. When the infusion solution X stored in the storage space 2*a* is administered to a living body from the filling port 3 through the tube portion 14 (to be described), the infusion solution X in the storage space 2*a* decreases. After that, the film body 51 returns from the state illustrated in FIG. 7 to the state illustrated in FIGS. 5 and 6 by the self-weight of the infusion solution X or resilience of the film body 51 itself. That is to say, because the film body 51 enters the recess 21 from the opening of the recess 21 toward the bottom surface 21*a* in the state in which the infusion solution X is not stored in the storage space 2*a*, the volume of the storage space 2*a* is reduced with a reduction in amount of the infusion solution X filled in the storage space 2*a*. Accordingly, most of the infusion solution X stored in the storage space 2*a* is easily fed through the filling port 3. In other words, it is possible to reduce an amount of the infusion solution X remaining in the storage space 2*a*** when administrating the infusion solution X.

In addition, in the state in which the infusion solution X is not stored in the storage space **2*a*, the film body 51 of this embodiment enters the recess 21 from the opening of the recess 21 toward the bottom surface 21*a* but is not in contact with the bottom surface 21*a*. Such a configuration prevents the film body 51 and the bottom surface 21*a* from closely adhering and sticking to each other. Accordingly, it is possible to prevent an increase in resistance when the infusion solution X is filled into the storage space 2*a***.

As illustrated in FIG. 8, the peripheral edge 52 of this embodiment includes a fixing portion 53, a cover portion 54, and a reinforcing portion 55.

The fixing portion 53 covers the end surface 33 of the opening end 40 of the case 10 and is fixed to the end surface 33. More specifically, the fixing portion 53 of this embodiment is a part bonded to the end surface 33. The film body 51 is located closer to the recess 21 than the fixing portion 53. More specifically, the film body 51 of this embodiment is continuous with the fixing portion 53 on the side closer to the recess 21. The cover portion 54 covers the second side surface 32 of the opening end 40 of the case 10 and is not fixed to the second side surface 32. The cover portion 54 of this embodiment is located on the side opposite to the recess 21 with respect to the fixing portion 53. More specifically, the cover portion 54 of this embodiment is continuous with the fixing portion 53 on the side opposite to the recess 21. The reinforcing portion 55 protrudes from the cover portion 54 in an out-of-plane direction of the second side surface 32 of the opening end 40 of the case 10. More specifically, the reinforcing portion 55 of this embodiment protrudes from the cover portion 54 in a flange shape.

The fixing structure for the opening end 40 of the case 10 and the film structure 12 will be described later in detail.

As illustrated in FIGS. 1 to 7, the lid 13 opens and closes the case body 11 between a state of uncovering the film structure 12 and a state of covering the film structure 12. Hereinafter, for the purpose of illustration, a state in which the lid 13 uncovers the film structure 12 (see, for example, FIG. 3) will be simply referred to as "open state." A state in which the lid 13 covers film structure 12 (see, for example, FIG. 2) will be simply referred to as "closed state."

The lid 13 is in the open state when the infusion solution X is filled into the storage space **2*a*. For this reason, even when bubbles enter the storage space 2*a* while the infusion solution X is filled into the storage space 2*a*, the film structure 12 is pushed from the outside and easily deformed. Therefore, as compared with a configuration in which the storage space 2*a* is completely surrounded by a member harder than the film structure 12 such as the case body 11, the bubbles in the storage space 2*a* are easily moved while the storage space 2*a*** is filled with the infusion solution X.

Furthermore, as described above, the storage space **2*a* of this embodiment is formed by covering the opening of the recess 21 in the case body 11 of the case 10 with the film structure 12. Therefore, as compared with a configuration in which the inner wall defining the storage space 2*a* consists of a flexible bag, it is possible to restrict the deformation of the inner wall of the storage space 2*a* within one part constituted by the film structure 12. In other words, the deformation of the inner wall of the storage space 2*a* is regulated to a desired aspect. Accordingly, it is possible to prevent local large deformation at an unintended position of the storage space 2*a* due to a pushing force applied to move the bubbles, thereby preventing accumulation of the bubbles. That is to say, it is possible to move the bubbles in the storage space 2*a*** more easily.

In addition, after the storage space **2*a* is filled with the infusion solution X, the lid 13 is brought to the closed state so as to protect the film structure 12 and prevent leakage of the infusion solution X due to perforation or the like and also to prevent a patient using the infusion pump 100 from taking out the infusion solution X such as liquid medicine in the storage space 2***a*.

The lid 13 of this embodiment is rotatably attached to the case body 11 by the hinge portion 15. With this configuration, the lid 13 is rotated by the hinge portion 15 relative to the case body 11 and changes between the open state and the closed state, thereby opening and closing the case body 11.

More specifically, the lid 13 of this embodiment includes a top plate portion 13*a* that covers the film structure 12 in the closed state and a side plate portion 13*b* that rises in a thickness direction of the top plate portion 13*a* from the outer edge of the top plate portion 13*a*. The top plate portion 13*a* faces the bottom plate portion 11*a* of the case body 11 in the closed state of the lid 13. Therefore, the film structure 12 is interposed between the bottom plate portion 11*a* of the case body 11 and the top plate portion 13*a* of the lid 13 in the closed state of the lid 13. In the closed state of the lid 13, the side plate portion 13*b* of the lid 13 and the side plate portion 11*b* of the case body 11 cover the periphery of the storage space 2*a* in a direction perpendicular to the thickness direction of the bottom plate portion 11*a* and the top plate portion 13*a*. That is to say, the lid 13 brought to the closed state causes the storage space 2*a* to be surrounded by the case body 11 and the lid 13.

More specifically, the side plate portion 13*b* of the lid 13 of this embodiment includes a first plate portion 13*b*1 that constitutes a train of side walls together with the first plate portion 11*b*1 of the case body 11. Furthermore, the side plate portion 13*b* of the lid 13 of this embodiment includes a second plate portion 13*b*2 that constitutes a train of side walls together with the second plate portion 11*b*2 of the case body 11. Still further, the side plate portion 13*b* of the lid 13 of this embodiment includes a third plate portion 13*b*3 that constitutes a train of side walls together with the fourth plate portion 11*b*4 of the case body 11. The first plate portion 13*b*1 and the second plate portion 13*b*2 of the lid 13 are provided with the locking claws 41 that are caught on the catches 42 of the first plate portion 11*b*1 and the second plate portion 11*b*2 of the case body 11 in the closed state of the lid 13. The third plate portion 13*b*3 of the lid 13 is connected to the fourth plate portion 11*b*4 of the case body 11 via the hinge portion 15.

The lid 13 of this embodiment is formed of a material similar to one used in the case body 11. In addition, the lid 13 of this embodiment is preferably thicker than the film structure 12 at any position. In terms of flexural rigidity, the lid 13 is also preferably larger than the film structure 12. With such a configuration, the film structure 12 is prevented from being pushed through the lid 13 and deformed in the closed state, that is, while the lid 13 covers the film structure 12.

The tube portion 14 is connected to the case body 11, enabling filling of the infusion solution X through the filling port 3. As described above, one end of the tube portion 14 of this embodiment is connected to the proximal side of the cylindrical portion 22 (see FIG. 3) via the L-shaped connecting tube portion 23 (see FIG. 2). Connecting a syringe, for example, to the other side of the tube portion 14 makes it possible to fill the storage space 2*a* with the infusion solution X through the tube portion 14.

In addition, in the use of the infusion pump 100, the tube portion 14 is employed as a part of an infusion tube that administers the infusion solution X filled in the storage space 2*a* to the living body. In other words, the infusion pump 100 illustrated in FIG. 1 causes a peristaltic motion of the tube portion 14 to feed the downstream side of the flow path with the infusion solution X discharged into the tube portion 14 from the storage space 2*a* through the filling port 3. On the downstream side of the flow path in the tube portion 14, for example, there is an indwelling needle placed inside the living body, and the infusion solution X is administered to the living body through this indwelling needle.

Fixing Structure for Case 10 and Film Structure 12

Next, the fixing structure for the case 10 and the film structure 12 will be described with reference to FIG. 8. FIG. 8 is an enlarged view of parts within a circle indicated by broken lines in FIG. 5. That is to say, FIG. 8 is an enlarged view of the opening end 40 of the case 10 and the surroundings thereof illustrated in FIG. 5.

As described above, the case 10 includes the opening end 40 that defines the opening of the recess 21. The opening end 40 includes the first side surface 31, the second side surface 32, and the end surface 33. The first side surface 31 faces the inside of the recess 21. The second side surface 32 is located on the side opposite to the first side surface 31. The end surface 33 connects the first side surface 31 and the second side surface 32. The opening end 40 extends endlessly. The inner edge of the endless end surface 33 closer to the recess 21 is continuous with the first side surface 31. The outer edge of the endless end surface 33 on the side opposite to the recess 21 is continuous with the second side surface 32.

Figure 11:
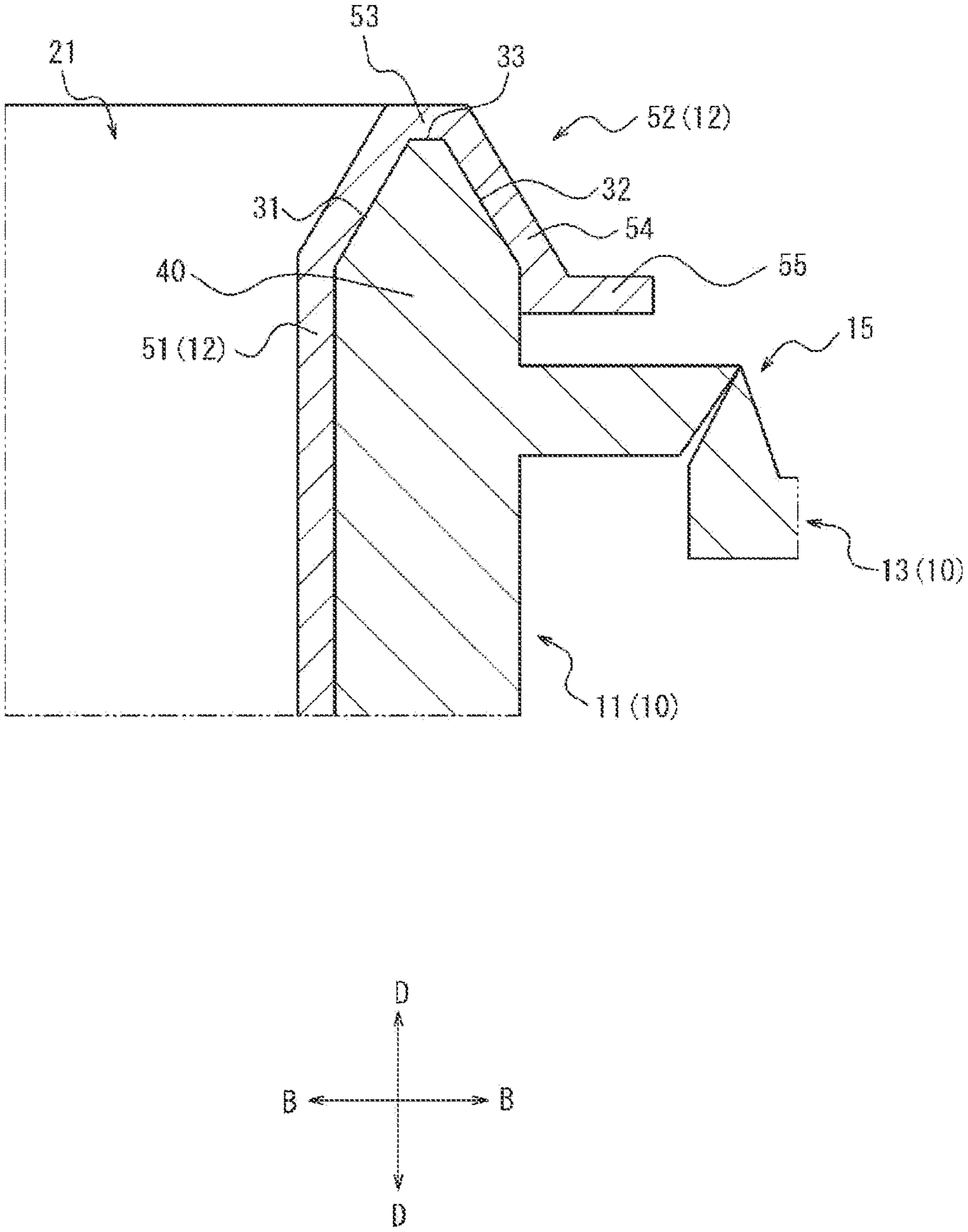
FIG. 11 is a view illustrating a modification of the case and the film structure illustrated in FIG. 8.

In this embodiment, the first side surface 31 and the second side surface 32 face each other and extend in substantially parallel but are not limited to this configuration (see FIG. 11).

As described above, the film structure 12 includes the film body 51 and the peripheral edge 52. Fixing the peripheral edge 52 to the opening end 40 over the entire region of the endless opening end 40 causes the film structure 12 to be fixed to the case 10.

Furthermore, as described above, the peripheral edge 52 includes the fixing portion 53 and the cover portion 54. The fixing portion 53 covers the end surface 33 and is fixed to the end surface 33. More specifically, the fixing portion 53 of this embodiment is a part bonded to the end surface 33. The fixing portion 53 of this embodiment has a hollow plate-shaped outline in which both ends of a belt-shaped film in a width direction are connected in an endless manner to constitute the inner edge and the outer edge. The cover portion 54 covers the second side surface 32 and is not fixed to the second side surface 32. In other words, the cover portion 54 covers the second side surface 32 but is not bonded to the second side surface 32 by welding or the like. The cover portion 54 of this embodiment is continuous with the fixing portion 53 on the side of the fixing portion 53 opposite to the recess 21. More specifically, the cover portion 54 of this embodiment protrudes from the outer edge of the hollow plate-shaped fixing portion 53 in a direction perpendicular to the fixing portion 53. The cover portion 54 of this embodiment has a cylindrical outline in which both side surfaces of a belt-shaped film in a thickness direction are connected in an endless manner to constitute the inner surface and the outer surface.

Because the film structure 12 includes such a cover portion 54, an unintended external force is hard to act on the fixing portion 53 of the film structure 12. In a case where the film structure 12 does not include the cover portion 54, when an unintended external force acts on the film structure 12 from the second side surface 32 of the case 10, it is likely to cause an external force that separates the fixing portion 53 from the end surface 33. In contrast, in a case where the film structure 12 includes the cover portion 54, an external force is likely to act on the cover portion 54. Accordingly, the external force tends to be used for deformation of the cover portion 54, and the fixing portion 53 is prevented from being affected by an unintended external force. With this configuration, an external force that separates the fixing portion 53 from the end surface 33 (for example, an external force that causes peeling) is prevented from acting on the fixing portion 53. Such a function makes it difficult to weaken a fixed state between the end surface 33 of the case 10 and the fixing portion 53 of the film structure 12, which prevents a decrease in airtightness and liquid tightness between the end surface 33 of the case 10 and the fixing portion 53 of the film structure 12. In other words, it is possible to enhance protectiveness of mutually fixed portions in the case 10 and the film structure 12 that define the storage space 2*a*.

Furthermore, the cover portion 54 of the film structure 12 may be used for aligning the end surface 33 of the opening end 40 of the case 10 and the fixing portion 53 before being fixed to the end surface 33. That is to say, the film structure 12 may be fixed to the end surface 33 while being positioned to cover the end surface 33 and the second side surface 32 in the opening end 40 of the case 10. With this configuration, because the cover portion 54 of the film structure 12 abuts on the second side surface 32 of the opening end 40 of the case 10, the fixing portion 53 of the film structure 12 before being fixed to the end surface 33 is prevented from being misaligned and falling in the recess 21. Accordingly, it is possible to easily fix the end surface 33 of the opening end 40 of the case 10 and the fixing portion 53 of the film structure 12. In other words, using the cover portion 54 of the film structure 12 as described above enables efficient fixing of the case 10 and the film structure 12.

More specifically, in this embodiment, the end surface 33 of the opening end 40 of the case 10 includes a base surface 33*a* and a rib-shaped protruding surface 33*b* protruding from the base surface 33*a* and bonded to the fixing portion 53 of the film structure 12 by welding. The protruding surface 33*b* of this embodiment is disposed in a central portion of the end surface 33 in a width direction B. The width direction B of the end surface 33 is perpendicular to the extending direction of the end surface 33 extending endlessly, that is, in this embodiment, a thickness direction of the side plate portion 11*b* (see FIGS. 3 to 7). Therefore, in the inner edge of the end surface 33 of this embodiment, the base surface 33*a* is continuous with the first side surface 31. Furthermore, in the outer edge of the end surface 33 of this embodiment, the base surface 33*a* is continuous with the second side surface 32.

As illustrated in FIG. 8, in this embodiment, the fixing portion 53 of the film structure 12 is bonded to the opening end 40 of the case 10 only at the top of the protruding surface 33*b* of the end surface 33. In other words, the fixing portion 53 of this embodiment is not bonded to the base surface 33*a*. With such a protruding surface 33*b* having the top bonded to the fixing portion 53, a sealing position (sealing line) between the end surface 33 of the case 10 and the fixing portion 53 of the film structure 12 is clear, which facilitates evaluation of sealing properties. The protruding surface 33*b* has a protruding height H of, for example, 0.1 mm to 0.3 mm from the base surface 33*a*. A gap may be formed between the fixing portion 53 and the base surface 33*a*. This gap may be, for example, 0.05 mm to 0.1 mm.

As described above, the protruding surface 33*b* of the end surface 33 of this embodiment is located at the central portion of the end surface 33 in the width direction B but is not limited to this configuration. The protruding surface 33*b* may be located at an end of the end surface 33 in the width direction B.

As illustrated in FIG. 8, the film structure 12 of this embodiment further includes the reinforcing portion 55 protruding from the cover portion 54 in the out-of-plane direction of the second side surface 32. The out-of-plane direction of the second side surface 32 intersects the second side surface 32. Such a reinforcing portion 55 makes it possible to enhance the flexural strength of the cover portion 54 in the out-of-plane direction of the second side surface 32. That is to say, in this embodiment, it is possible to increase the flexural strength in the thickness direction of the belt-shaped film constituting the cover portion 54. Accordingly, even when an external force acts on the reinforcing portion 55, the external force tends to be used for deformation of the reinforcing portion 55 relative to the cover portion 54, whereby the fixing portion 53 and the cover portion 54 are prevented from being affected by an unintended external force. With this configuration, an external force that separates the fixing portion 53 from the end surface 33 (for example, an external force that causes peeling) is further prevented from acting on the fixing portion 53. Such a function makes it even more difficult to weaken the fixed state between the end surface 33 of the case 10 and the fixing portion 53 of the film structure 12, which further prevents a decrease in airtightness and liquid tightness between the end surface 33 of the case 10 and the fixing portion 53 of the film structure 12. In other words, it is possible to further enhance protectiveness of the mutually fixed portions in the case 10 and the film structure 12 that define the storage space 2*a*.

As illustrated in FIG. 8, the reinforcing portion 55 of this embodiment protrudes in a flange shape from the cover portion 54, being in substantially parallel with the thickness direction of the belt-shaped film constituting the cylindrical cover portion 54, but is not limited to this configuration. The reinforcing portion 55 may protrude in another direction as long as it is in the out-of-plane direction of the second side surface 32. In addition, the reinforcing portion 55 of this embodiment protrudes from one end in the width direction of the belt-shaped film constituting the cylindrical cover portion 54 but is not limited to this configuration. The reinforcing portion 55 may protrude from a central portion in the width direction of the belt-shaped film constituting the cylindrical cover portion 54. In this embodiment, the fixing portion 53 is connected to the other end in the width direction of the belt-shaped film constituting the cylindrical cover portion 54.

Furthermore, as described above, the film structure 12 of this embodiment includes the film body 51. The film body 51 of this embodiment is located on the side of the fixing portion 53 closer to the recess 21. More specifically, the film body 51 of this embodiment is continuous with the fixing portion 53 on the side closer to the recess 21. As described above, the film body 51 of this embodiment enters the recess 21 from the opening of the recess 21 toward the bottom surface 21*a* in a state in which the infusion solution X is not stored in the storage space 2*a* (see FIGS. 3, 5, and 6). The film body 51 of this embodiment is deformed by storing the infusion solution X in the storage space 2*a* (see FIGS. 4 and 7). With such a film body 51, as described above, most of the infusion solution X stored in the storage space 2*a* is easily fed through the filling port 3. That is to say, it is possible to reduce an amount of the infusion solution X remaining in the storage space 2*a* when administrating the infusion solution X.

Furthermore, as illustrated in FIG. 8, a part adjacent to the fixing portion 53 in the film body 51 extends along the first side surface 31 of the opening end 40 of the case 10 in the state in which the infusion solution X is not stored in the storage space 2*a*. In other words, the film structure 12 of this embodiment sandwiches the opening end 40 of the case 10 with the part adjacent to the fixing portion 53 in the film body 51 extending along the first side surface 31 of the opening end 40 of the case 10 and the cover portion 54 covering the second side surface 32 of the opening end 40 of the case 10. Therefore, in the film structure 12 of this embodiment, the film body 51 may be used for aligning the end surface 33 of the opening end 40 of the case 10 and the fixing portion 53 before being fixed to the end surface 33. In other words, sandwiching the opening end 40 of the case 10 between the part adjacent to the fixing portion 53 in the film body 51 and the cover portion 54 makes it possible to easily align the end surface 33 and the fixing portion 53 of the film structure 12 before being fixed to the end surface 33. Accordingly, it is possible to fix the end surface 33 of the opening end 40 of the case 10 and the fixing portion 53 of the film structure 12 more easily. More specifically, using the part adjacent to the fixing portion 53 in the film body 51 of the film structure 12 as described above enables more efficient fixing of the case 10 and the film structure 12.

The side surface 21*b* of the recess 21 of the case 10 includes the first side surface 31 of the opening end 40. In the state in which the infusion solution X is not stored in the storage space 2*a*, the film body 51 of this embodiment covers a predetermined region including the first side surface 31 of the side surface 21*b* of the recess 21. In this manner, covering the region including the first side surface 31 of the side surface 21*b* with the film body 51 enhances the aforementioned effect. That is to say, it is possible to further reduce the amount of the infusion solution X remaining in the storage space 2*a* without being fed. Furthermore, the aforementioned fixing is made more efficient.

The side surface 21*b* covered with the film body 51 is not particularly limited in length in a depth direction D of the recess 21. The longer the length of the side surface 21*b* covered with the film body 51 in the depth direction D of the recess 21, the larger the capacity of the storage space 2*a*. However, the length of the film body 51 in the depth direction D also increases, and in a case where the film structure 12 does not include the cover portion 54, before the fixing portion 53 is fixed to the end surface 33 of the opening end 40 of the case 10, the fixing portion 53 is likely to slip from the end surface 33 and fall in the recess 21, which makes it difficult to fix the fixing portion 53 and the end surface 33. In contrast, in a case where the film structure 12 includes the cover portion 54, even when the length of the side surface 21*b* covered with the film body 51 in the depth direction D of the recess 21 increases, the fixing portion 53 and the end surface 33 are easily aligned. Accordingly, the film structure 12 including the cover portion 54 easily achieves both capacity expansion of the storage space 2*a* in the depth direction D and efficiency in fixing the film structure 12 to the case 10.

The length of the side surface 21*b* covered with the film body 51 in the depth direction D of the recess 21 is not particularly limited as described above, but in this embodiment, the predetermined region of the side surface 21*b* of the recess 21 covered with the film body 51 has a length in the depth direction D set to 0.5 mm or more. In this embodiment, setting the length to 0.5 mm or more makes it easier to obtain the various effects generated by the film body 51 covering at least a part of the side surface 21*b* of the recess 21.

Furthermore, the predetermined region of the side surface 21*b* of the recess 21 covered with the film body 51 has a length in the depth direction D of the recess 21 preferably accounting for 70% to 98%, more preferably 80% to 98%, and particularly preferably 90% to 98% of a maximum depth T (see FIGS. 5 and 6), or the length of the recess 21 in the depth direction D. Setting the ratio of the length to 70% or more reduces an amount of air entering the storage space 2*a* not storing the infusion solution X and reduces an amount of the infusion solution X remaining in the storage space 2*a* at the time of the administration. In addition, setting the ratio of the length to 98% or less ensures a gap between the film body 51 and the inner surface (the bottom surface 21*a* and the side surface 21*b*) of the recess 21 in the state in which the infusion solution X is not stored in the storage space 2*a*. Accordingly, it is possible to prevent an increase in resistance when the infusion solution X is filled into the storage space 2*a*. In this embodiment, the predetermined region of the side surface 21*b* of the recess 21 covered with the film body 51 has a length in the depth direction D set to 30 mm or less from a viewpoint of satisfying the above ratio of the length.

Furthermore, as illustrated in FIG. 8, the hinge portion 15 of this embodiment is disposed on a side closer to the bottom surface 21*a* of the recess 21 in the depth direction D of the recess 21 than the cover portion 54 of the film structure 12. With this configuration, even when a gap is formed at the position of the hinge portion 15, the cover portion 54 of the film structure 12 and the fixing portion 53 located closer than the cover portion 54 to the opposite side of the bottom surface 21*a* of the recess 21 in the depth direction D are prevented from being pricked unintendedly by a needle through the gap. Accordingly, it is possible to prevent impairment of airtightness and liquid tightness of the storage space 2*a* due to, for example, an unintended hole in the film structure 12 caused by a needle prick. In other words, it is possible to further enhance protectiveness of the mutually fixed portions in the case 10 and the film structure 12 that define the storage space 2*a*.

As illustrated in FIG. 8, the case body 11 and the lid 13 of this embodiment are molded in an integrated manner from the same resin material. The hinge portion 15 is a living hinge including a part connected to the case body 11 and the lid 13. However, the case body 11 and the lid 13 may be separate members. In such a case, the hinge portion 15 may be a hinge or another hinge member that relatively connects members constituting the case body 11 and the lid 13 in a rotatable manner.

Figure 9:
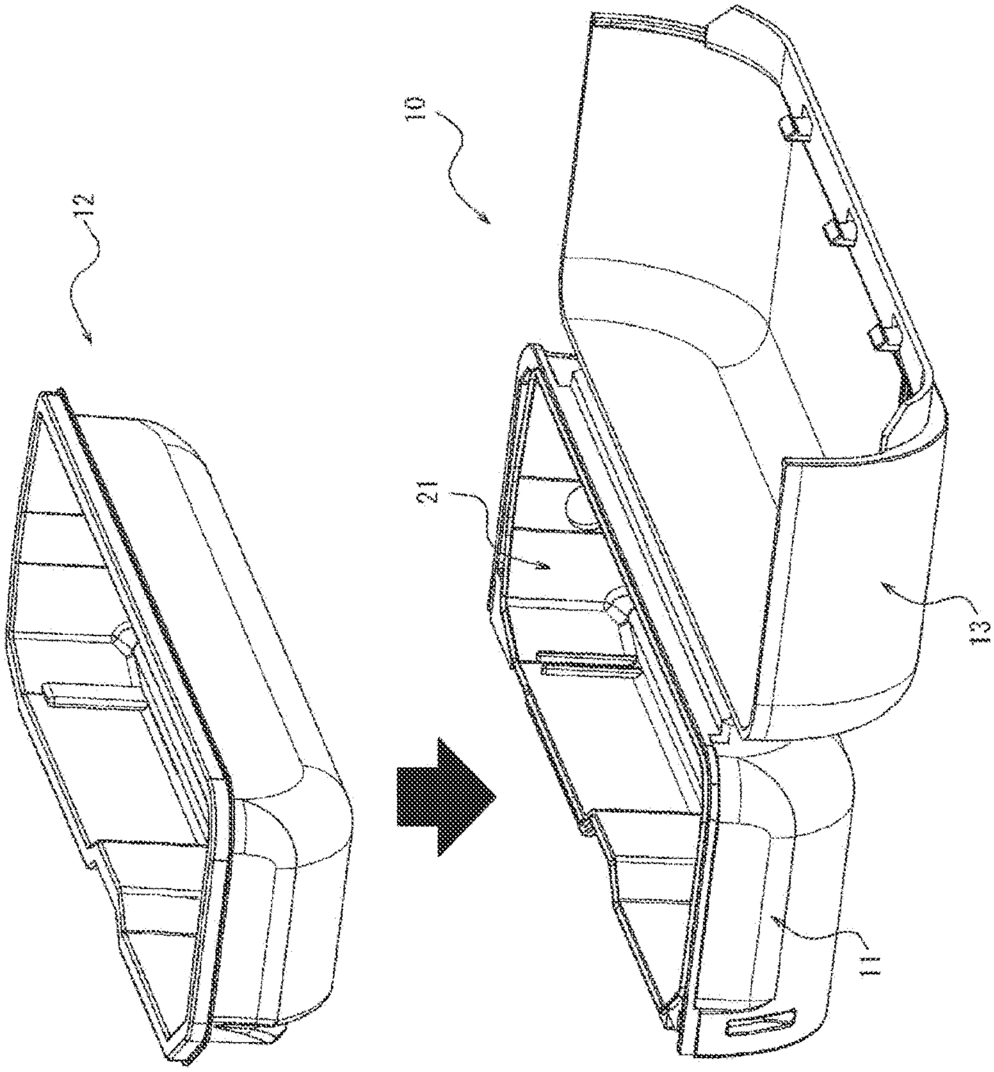
FIG. 9 is a perspective view illustrating a state before a film structure is fixed to a case.
Figure 10:
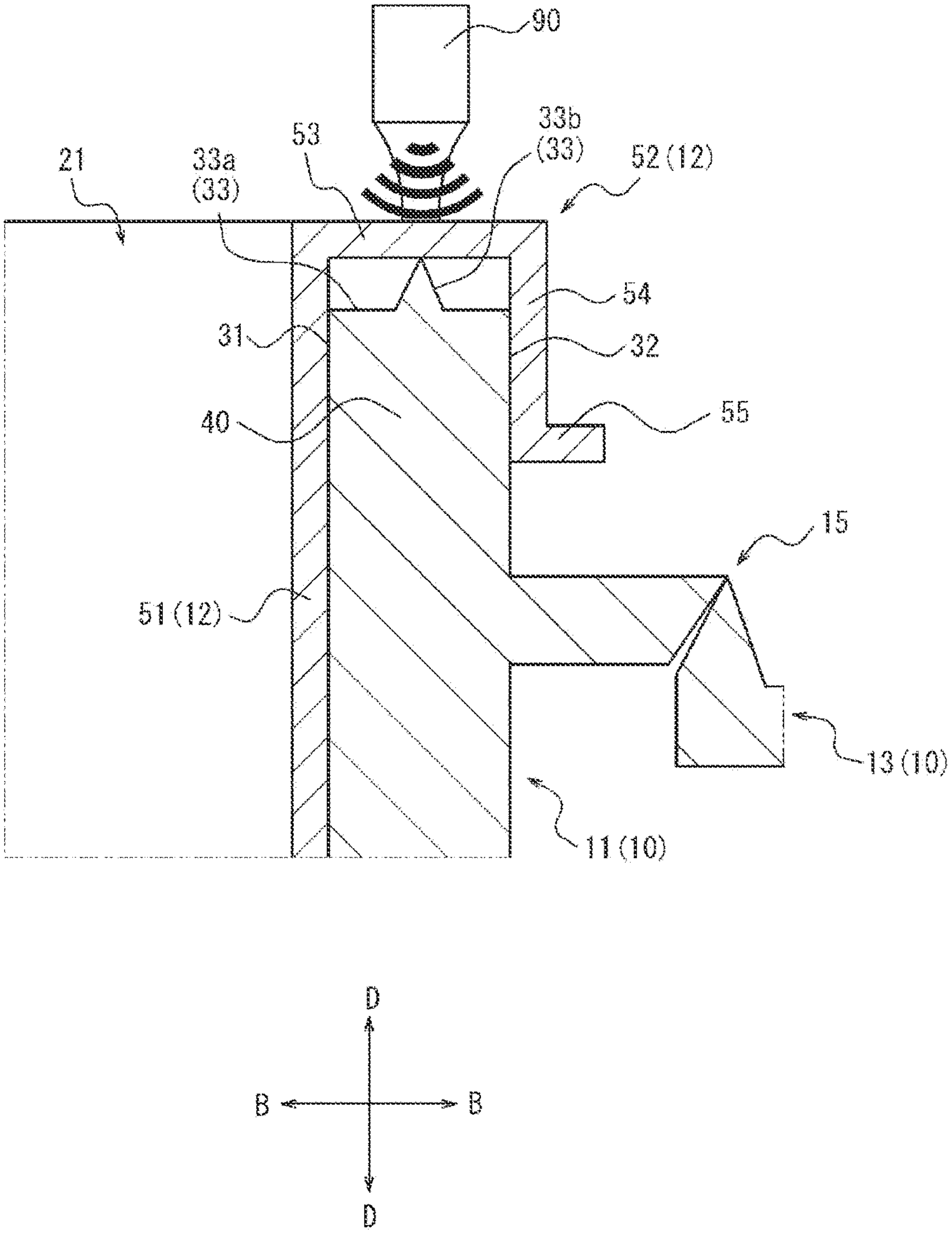
FIG. 10 is a view illustrating how to fix the film structure to the case.

Lastly, a method for fixing the film structure 12 to the case 10 in the method for manufacturing the infusion cartridge 2 will be described with reference to FIGS. 9 and 10. FIG. 9 illustrates a state before the film structure 12 is fixed to the case 10. FIG. 10 is a view illustrating how to fix the film structure 12 to the case 10. When the fixing illustrated in FIG. 10 is completed, the fixed state illustrated in FIG. 8 is obtained. Although the outlines of the case 10 and the film structure 12 illustrated in FIG. 9 are different in detail from the outlines of the case 10 and the film structure 12 illustrated in FIGS. 1 to 7, the fixing structure for the case 10 and the film structure 12 is similar to the structure illustrated in FIGS. 1 to 7.

As illustrated in FIG. 9, first, the film structure 12 is disposed in the recess 21 of the case body 11 of the case 10 (see a thick arrow in FIG. 9).

Accordingly, as illustrated in FIG. 10, the fixing portion 53 and the cover portion 54 of the film structure 12 are caught on the opening end 40 of the case 10. For this reason, as described above, it is possible to align the end surface 33 of the opening end 40 of the case 10 and the fixing portion 53 of the film structure 12 with ease.

After the alignment, ultrasonic vibration and pressure are simultaneously applied from an oscillator (not illustrated) via a horn 90 as illustrated in FIG. 10. This operation causes the protruding surface 33*b* of the end surface 33 to fuse, whereby the protruding surface 33*b* of the end surface 33 of the case 10 and the fixing portion 53 of the film structure 12 are welded together. In this manner, it is possible to fix the case 10 and the film structure 12 with ease.

The infusion cartridge, the infusion pump, and the method for manufacturing the infusion cartridge according to this disclosure are not limited to the specific configurations illustrated in the embodiment, and various modifications, changes, and combinations are possible without departing from the claims.

For example, the case body 11 of the infusion cartridge 2 may be a single member or may include a plurality of members. The case body 11 may include, for example, a box structure that defines the recess 21 and a plate structure attached to a side surface of the box structure and constituting the tube holder 30 (see FIG. 2). In the case body 11 illustrated in FIG. 9, the plate structure is omitted. That is to say, FIG. 9 illustrates only the box structure of the case body 11 that includes the box structure and the plate structure. The case body 11 may have the box structure and the plate structure formed in an integrated manner as a single member.

In addition, in the embodiment, the first side surface 31 and the second side surface 32 of the opening end 40 of the case 10 are surfaces parallel to each other but are not limited to this configuration. As illustrated in FIG. 11, the first side surface 31 and the second side surface 32 may be inclined surfaces that are inclined in such a manner that a distance between the surfaces gradually decreases toward the end surface 33. Alternatively, the first side surface 31 and the second side surface 32 may be surfaces not parallel to each other and different from the inclined surfaces illustrated in FIG. 11. Furthermore, the cover portion 54 of the film structure 12 of the embodiment is parallel to a film thickness direction of the fixing portion 53 but is not limited to this configuration. As illustrated in FIG. 11, the cover portion 54 of the film structure 12 may be a part inclined along the second side surface 32, not being parallel to the film thickness direction of the fixing portion 53.

INDUSTRIAL APPLICABILITY

This disclosure relates to an infusion cartridge, an infusion pump, and a method for manufacturing an infusion cartridge.

REFERENCE SIGNS LIST

1 PUMP BODY
2 INFUSION CARTRIDGE
2*a* STORAGE SPACE
3 FILLING PORT
4 VENTILATION PORT
5 VENTILATION FILTER
10 CASE
11 CASE BODY
11*a* BOTTOM PLATE PORTION
11*b* SIDE PLATE PORTION
11*b*1 FIRST PLATE PORTION
11*b*2 SECOND PLATE PORTION
11*b*3 THIRD PLATE PORTION
11*b*4 FOURTH PLATE PORTION
12 FILM STRUCTURE
13 LID
13*a* TOP PLATE PORTION
13*b* SIDE PLATE PORTION
13*b*1 FIRST PLATE PORTION
13*b*2 SECOND PLATE PORTION
13*b*3 THIRD PLATE PORTION
14 TUBE PORTION
15 HINGE PORTION
18 CYLINDRICAL PORTION
19 CAP
20 EXTENDED PORTION
21 RECESS
21*a* BOTTOM SURFACE
21*b* SIDE SURFACE
22 CYLINDRICAL PORTION
23 CONNECTING TUBE PORTION
30 TUBE HOLDER
31 FIRST SIDE SURFACE
32 SECOND SIDE SURFACE
33 END SURFACE
33*a* BASE SURFACE
33*b* PROTRUDING SURFACE
40 OPENING END
41 LOCKING CLAW
42 CATCH
51 FILM BODY
52 PERIPHERAL EDGE
53 FIXING PORTION
54 COVER PORTION
55 REINFORCING PORTION
90 HORN
100 INFUSION PUMP
120 DISPLAY UNIT
130 OPERATION UNIT
131 FAST DELIVERY SWITCH
132 START SWITCH
133 STOP SWITCH
134 POWER SUPPLY SWITCH
140 LIQUID FEEDING UNIT
B WIDTH DIRECTION IN END SURFACE
D DEPTH DIRECTION IN RECESS
H PROTRUDING HEIGHT OF PROTRUDING SURFACE FROM BASE SURFACE
T MAXIMUM DEPTH OF RECESS
X INFUSION SOLUTION

The invention claimed is:

1. An infusion cartridge comprising:
a case provided with a recess; and
a film structure that has flexibility, covers an opening of the recess, and, together with the recess, defines a storage space configured to store an infusion solution, wherein:
the case includes an opening end that defines the opening of the recess, the opening end including:
a first side surface facing inside of the recess,
a second side surface located on a side opposite to the first side surface, and
an end surface connecting the first side surface and the second side surface, and
the film structure comprises:
a fixing portion that covers the end surface and is fixed to the end surface, and
a cover portion that covers the second side surface and is not fixed to the second side surface.

2. The infusion cartridge according to claim 1, wherein the film structure comprises a reinforcing portion that protrudes outward from the cover portion in a direction traverse to the second side surface.

3. The infusion cartridge according to claim 1, wherein:

the film structure comprises a film body that is located on a recess side of the fixing portion and is deformed when the infusion solution is stored in the storage space, and the film body enters the recess from the opening of the recess toward a bottom surface of the recess in a state in which the infusion solution is not stored in the storage space.

4. The infusion cartridge according to claim 3, wherein:

the recess has a side surface that includes the first side surface of the opening end, and the film body covers a predetermined region including the first side surface of the side surface of the recess in a state in which the infusion solution is not stored in the storage space.

5. The infusion cartridge according to claim 4, wherein the predetermined region has a length in a depth direction of the recess in a range of 70% to 98% of a maximum depth of the recess.

6. The infusion cartridge according to claim 1, wherein:

the case comprises:

a case body provided with the recess, and a lid rotatably attached to the case body via a hinge portion, the lid is rotatable relative to the case body by the hinge portion to open and close the case body between a state of uncovering the film structure and a state of covering the film structure, and the hinge portion is disposed on a bottom surface side of the cover portion in a depth direction of the recess.

7. The infusion cartridge according to claim 1, wherein the case is provided with a ventilation port through which a gas in the storage space is dischargeable.

8. An infusion pump comprising:

an infusion cartridge comprising:

a case provided with a recess, and a film structure that has flexibility, covers an opening of the recess, and, together with the recess, defines a storage space configured to store an infusion solution, wherein:

the case includes an opening end that defines the opening of the recess, the opening end including:

a first side surface facing inside of the recess, a second side surface located on a side opposite to the first side surface, and an end surface connecting the first side surface and the second side surface, and the film structure comprises:

a fixing portion that covers the end surface and is fixed to the end surface, and a cover portion that covers the second side surface and is not fixed to the second side surface; and a pump body to which the infusion cartridge is attachable.

9. A method for manufacturing an infusion cartridge, the method comprising:

a step of covering an opening of a recess of a case with a film structure having flexibility to define a storage space between the recess of the case and the film structure, the storage space being configured to store an infusion solution, wherein:

the case includes an opening end that defines the opening of the recess, the opening end including:

a first side surface facing inside of the recess, a second side surface facing a side opposite to the inside of the recess, and an end surface connecting the first side surface and the second side surface, and in the step of covering the opening, the film structure is fixed to the end surface while being positioned to cover the end surface and the second side surface in the opening end of the case.

* * * * *